(12) United States Patent
Ishimaru et al.

(10) Patent No.: US 6,797,503 B1
(45) Date of Patent: Sep. 28, 2004

(54) ENZYME

(75) Inventors: Kaori Ishimaru, Kyoto (JP); Masayuki Yagi, Kyoto (JP); Satoshi Yonehara, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/913,874

(22) PCT Filed: Feb. 21, 2000

(86) PCT No.: PCT/JP00/00984

§ 371 (c)(1),
(2), (4) Date: Oct. 11, 2001

(87) PCT Pub. No.: WO00/50579

PCT Pub. Date: Aug. 31, 2000

(30) Foreign Application Priority Data

Feb. 22, 1999 (JP) .............................. 11-042926
Apr. 12, 1999 (JP) ........................... 11-142186

(51) Int. Cl.$^7$ ............................. C12N 9/52; C12N 9/48; C12N 9/50; C12Q 1/37
(52) U.S. Cl. ........................ 435/220; 435/23; 435/212; 435/219
(58) Field of Search ................................ 435/212, 219, 435/220, 23

(56) References Cited

U.S. PATENT DOCUMENTS 5,370,990 A    12/1994    Staniford et al.

FOREIGN PATENT DOCUMENTS

| EP | 0 526 150 A1 | 2/1993 |
| EP | 0 678 576 A2 | 10/1995 |
| JP | 50-19628 | 7/1975 |
| JP | 63-279782 | 11/1988 |
| JP | 5-192193 | 8/1993 |
| JP | 7-289253 | 11/1995 |
| WO | 97/20039 | * 6/1997 |
| WO | 98/48043 | * 10/1998 |

OTHER PUBLICATIONS

Yoshida et al. "Primary structures of fungal frustosyl amino acid oxidases and their application to the measurement of glycated proteins" Eur. J. Biochem. vol. 242, pp 499–505, 1996.

Kenji Yamaoto "Microbial Endoglycosidases for Analyses of Oligosaccharide Chians in Glycoproteins" J. Biochem. vol. 116, pp 229–235, 1994.

Gerhardinger et al. "Isolation. Purification. and Characterization of an Amadori Product Binding Protein from a Pseudomonas sp. Soil Strain", The Journal of Biological Chemistry vol. 269, No. 44 pp 27297–27302, 1994.

Bisse et al "High–performance liquid chromatographic separation of human Haemoglobins" Journal of Chromatography, vol. 434, pp. 95–110, 1988.

Shin et al., "Identification of the protease producing bacteria to use fish metal wastewater and the producing conditions for the enzyme" Bull. Korean Fish Soc., vol. 22, No. 3, pp. 138–146, 1989.

F.W.J. Teale "Cleavage of the haem–protein link by acid methylethylketone" Biochim Biophys Acta 88, vol. 35, p. 543, 1959.

* cited by examiner

*Primary Examiner*—Sandra E. Saucier
(74) *Attorney, Agent, or Firm*—Merchant & Gould P.C.

(57) ABSTRACT

The present invention relates to a novel enzyme (α-GARE) which releases an amino acid residue having a glycated α-amino group (α-GA) from a glycated protein etc. and to bacterial strains producing the same. Examples of the bacterial strains include *Corynebacterium ureolyticum* KDK1002 (FERM P-17135) and *Pseudomonas alcaligenes* KDK1001 (FERM P-17133). The α-GARE is contained in the culture supernatant of these strains and α-GA can be released from a glycated peptide by using the same, as shown in FIG. 1.

5 Claims, 10 Drawing Sheets

Lane No. 1   Control FV
Lane No. 2   Controls Leu, Val, His
Lane No. 3   F 2 P degradation product
Lane No. 4   F 3 P degradation product Lane No. 1   F 2 P degradation product
Lane No. 2   F 5 P degradation product Lane No. 1   Control FV
Lane No. 2   Controls Leu, Val, His
Lane No. 3   F 2 degradation product
Lane No. 4   F 3 degradation product

ENZYME

TECHNICAL FIELD

The present invention relates to an enzyme.

BACKGROUND ART

Proteases are used in various industrial fields. For example, proteases are used for determining a glycated protein, e.g., glycated albumin, in serum, which can serve as a significant index for the diagnosis, treatment, etc. of diabetes.

Such determination of the glycated protein utilizing the protease can be carried out, for example, by degrading the glycated protein with the protease, reacting the resultant degradation product with a fructosyl amino acid oxidase (hereinafter, referred to as "FAOD"), and then determining oxygen consumption or hydrogen peroxide generation to find the amount of the glycated protein. Examples of the protease include those disclosed in JP 5(1993)-192193 A and JP 7(1995)-289253 A.

The above-mentioned protease pre-treatment of the glycated protein is conducted because FAOD and the like easily act on a glycated amino acid and a glycated peptide whereas they hardly act on the glycated protein itself. Particularly, since the glycated site of glycated hemoglobin (hereinafter, referred to as "HbA1c") is the N-terminal amino acid residue of the β-chain, there has been a demand for a protease capable of treating HbA1c so that FAOD easily can act on this site of the HbA1c.

DISCLOSURE OF THE INVENTION

Therefore, it is an object of the present invention to provide a novel enzyme capable of treating a glycated protein and a glycated peptide so that FAOD easily can act thereon.

First, among various FAODs, the inventors of the present invention have studied the mechanism of the action of the FAOD that acts on a glycated protein, glycated peptide, glycated amino acid, etc. in which a sugar is bound to an α-amino group. From this study, the inventors have found that such FAOD easily acts on the glycated amino acid in which a sugar is bound to an α-amino group whereas it hardly acts on the above glycated protein and glycated peptide. Based on this finding, the inventors have isolated various bacteria from nature, cultured them, and studied the enzymes produced by them. As a result, the inventors have succeeded in isolating the bacteria producing a novel enzyme capable of releasing an amino acid having a glycated α-amino group (α-Glycated Amino acid: hereinafter, referred to as "α-GA") from the glycated protein or glycated peptide in which sugar is bound to an α-amino group (an N-terminal amino group), thereby establishing the present invention. The novel enzyme (α-Glycated Amino acid Releasing Enzyme: hereinafter, referred to as "α-GARE") according to the present invention can release α-GA, for example, from the above glycated protein or glycated peptide. Hence, the determination of HbA1c using the FAOD that easily acts on α-GA can be made practical in clinical tests etc. by the use of this novel enzyme. The novel enzyme according to the present invention can be utilized not only for the determination of HbA1c but also in various application fields, e.g., for the determination of other glycated proteins. Furthermore, in addition to the catalytic functions of releasing α-GA, α-GARE of the invention may have other catalytic functions, e.g., the function of cleaving other peptide bonds. Examples of novel bacterial strains isolated by the present inventors include bacterial strains of the genus Corynebacterium and the genus Pseudomonas. However, it is to be noted that α-GARE according to the present invention is not limited to those derived from the strains of these genera.

The glycated amino acid released by α-GARE is not specifically limited as long as it has a glycated α-amino group. However, since the N-terminal valine residue is glycated in HbA1c as described above, the glycated amino acid released by α-GARE preferably is a glycated valine (hereinafter, referred to as "α-GV").

Examples of α-GARE according to the present invention include the following two types.

The first α-GARE (hereinafter, referred to as "α-GARE-1") is derived from the bacterial strain of the genus Corynebacterium and most preferably from *Corynebacterium ureolyticum* KDK1002. *Corynebacterium ureolyticum* KDK1002 was isolated from the soil novelly by the present inventors. *Corynebacterium ureolyticum* KDK1002 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17135 since Jan. 11, 1999. Bacteriological properties of this strain are as shown below.

(Morphological Characteristics)

This strain is a non-motile, rod-shaped bacterium (bacillus) of 0.8×1.2 μm.

(Culture Characteristics)

When cultured in an agar medium according to the usual method, the strain forms a colony that is circular in form and low convex in elevation. The colony is cream-colored.

| (Physiological Characteristics) | |
| --- | --- |
| Gram's stain: | positive |
| Oxygen requirement: | facultative anaerobic |
| Nitrate reduction: | − |
| Pyrazinamidase: | + |
| Pyrrolidonylarylamidase: | − |
| Alkaline phosphatase: | − |
| β-glucuronidase: | − |
| β-galactosidase: | − |
| α-glucosidase: | − |
| N-acetyl-β-glucosaminase: | − |
| Esculin (glucosidase): | − |
| Urease: | + |
| Gelatin degradation: | − |
| β-hemolysis: | − |
| Carbohydrate fermentability | |
| Glucose: | − |
| Ribose: | − |
| Xylose: | − |
| Mannitol: | − |
| Maltose: | − |
| Lactose: | − |
| Sucrose: | − |
| Glycogen: | − |

The second α-GARE (hereinafter, referred to as "α-GARE-2") is derived from the bacterial strain of the genus Pseudomonas and most preferably from *Pseudomonas alcaligenes* KDK1001. *Pseudomonas alcaligenes* KDK1001 also was isolated from the soil novelly by the present inventors. *Pseudomonas alcaligenes* KDK1001 has been deposited with the National Institute of Bioscience and Human Technology (NIBH), Agency of Industrial Science and Technology, Ministry of International Trade and Industry (1-3, Higashi 1-chome, Tsukuba-shi, Ibaraki 305-0046, JAPAN) under the Accession Number FERM P-17133 since Jan. 11, 1999. Bacteriological properties of this strain are as shown below.

(Morphological Characteristics)

This strain is a rod-shaped bacterium (bacillus) of 0.3×1.5 μm, which is motile by polar flagellums.

(Culture Characteristics)

When cultured in an agar medium according to the usual method, the strain forms a colony that is circular in form, low convex in elevation, with a smooth surface. The colony initially is translucent and then turns to light yellow. When cultured in the Mac Conkey's culture medium, the strain grows, albeit weakly. Further, at a culture temperature of 40° C., the strain does not grow at all.

| (Physiological Characteristics) | |
|---|---|
| Gram's stain: | negative |
| Oxygen requirement: | aerobic |
| Nitrate reduction: | + |
| Indole production: | − |
| Glucose acidification: | − |
| Arginine dihydrolase: | − |
| Urease: | − |
| Esculin hydrolysis: | + |
| Gelatin hydrolysis: | − |
| β-galactosidase: | + |
| Gas generation from glucose: | − |
| Substrate utilization | |
| Glucose: | + |
| L-arabinose: | + |
| D-mannose: | + |
| D-mannitol: | + |
| N-acetyl-D-gluconsamine: | − |
| Maltose: | + |
| Potassium gluconate: | + |
| n-capric acid: | + |
| Adipic acid: | − |
| DL-malic acid: | + |
| Sodium citrate: | − |
| Phenyl acetate: | − |

A method of determining a glycated protein or a glycated peptide according to the present invention includes: degrading a glycated protein or a glycated peptide with an enzyme; causing a redox reaction between the resultant degradation product and FAOD; and determining the redox reaction so as to determine the glycated protein or the glycated peptide. In this method, the novel enzyme (α-GARE) according to the present invention is used as the above enzyme. The type of the α-GARE used in this method is decided appropriately depending on the type, concentration, etc. of the glycated protein or glycated peptide to be determined. The α-GARE may be used alone or in combination of two or more types. The glycated protein or the like may be degraded by the pretreatment with another enzyme (e.g., protease) so that the α-GARE more easily can act thereon.

In the determination method according to the present invention, the redox reaction preferably is determined by measuring the amount of hydrogen peroxide produced by the redox reaction or the amount of oxygen consumed by the redox reaction. The amount of the hydrogen peroxide preferably is measured using a peroxidase and a substrate that develops color by oxidation (hereinafter, referred to as "chromogenic substrate"). The amount of the hydrogen peroxide can be determined not only by the above-mentioned enzymic method utilizing the peroxidase or the like but also by an electrical method, for example.

Examples of the chromogenic substrate include N-(carboxymethylaminocarbonyl)-4,4'-bis(dimethylamino) diphenylamine sodium (for example, the trade name "DA-64" available from Wako Pure Chemical Industries, Ltd.), orthophenylenediamine (OPD), and a substrate obtained by combining a Trinder's reagent and 4-aminoantipyrine. Examples of the above Trinder's reagent include phenols, phenol derivatives, aniline derivatives, naphthols, naphthol derivatives, and naphthylamine, naphthylamine derivatives. Further, in place of the above aminoantipyrine, it is possible to use aminoantipyrine derivatives, vanillin diamine sulfonic acid, methyl benzothiazolinone hydrazone (MBTH), sulfonated methyl benzothiazolinone hydrazone (SMBTH), and the like. Among these chromogenic substrates, N-(carboxymethylaminocarbonyl)-4,4'-bis(dimethylamino) diphenylamine sodium is particularly preferable.

In the determination method according to the present invention, a sample to be analyzed preferably is blood cells because determining HbA1c in blood cells is useful for diagnosis of diabetes as described above. However, the sample is not limited to the blood cells because blood components other than the blood cells (whole blood, plasma, serum, etc.); biological samples such as urine and spinal fluid; beverage such as juice; food such as soy sauce and sauce, etc. also contain glycated proteins. Also, an analyte to be determined is not limited to HbA1c and can be, for example, a glycated protein such as gelatin and casein or a glycated peptide.

A kit for determining a glycated protein or a glycated peptide according to the present invention includes a protease, FAOD, a peroxidase, and a substrate that is oxidized through a reaction with the peroxidase. In this determination kit, the protease comprises an α-GARE of the present invention. The determination method according to the present invention can be carried out rapidly and easily by using this kit. Also in this determination kit, the α-GARE may be used alone or in combination of two or more types.

In the determination kit according to the present invention, as the substrate to be oxidized, the chromogenic substrates described above preferably are used. Further, an analyte and a sample to be used in this kit also are as described above.

A method of producing α-GARE of the invention includes the step of culturing a novel bacterial strain of the invention. This method enables easy production of α-GARE according to the present invention.

It is preferable that the method of producing α-GARE of the present invention further includes the following purification steps (a) to (c):

(a) the step of removing the bacterial cells from the culture solution to prepare a supernatant;

(b) the step of precipitating the protein contained in the supernatant with ethanol; and (c) the step of separating the protein by chromatography.

The above purification steps are not specifically limited and may be performed along with other purification steps. Further, it is possible to perform, for example, the step (a) only; to perform the two or more steps; or to perform the same step repeatedly.

The α-GARE of the invention obtained through the above-mentioned culture of the bacterial strain may be used in the state of being contained in the culture solution or in the state of being purified. The α-GARE can be used regardless of its purification level as long as it can release α-GA from the glycated protein or the like. However, if purified, a specific activity of the α-GARE can be improved because the components other than the α-GARE in the culture solution are removed by the purification. Accordingly, the amount of the α-GARE to be used can be reduced, which facilitates the handling of the α-GARE. In addition, when the α-GARE is used for causing various reactions, influence given by the components other than the α-GARE can be avoided.

The genes encoding α-GARE of the present invention preferably are prepared by determining the amino acid sequence and the gene sequence of the α-GARE purified through the above purification steps. The genes encoding α-GARE of the invention are not limited to those necessary for the expression of the α-GARE. Examples of such genes include a DNA fragment, RNA, etc., which are used as a probe or primer, and a fragment synthesized chemically based on the gene sequence of the above α-GARE. Using such genes, a recombinant or the like may be prepared to produce α-GARE. The genes of α-GARE according to the present invention can be obtained, for example, in the following manner.

First, α-GARE of the invention is purified, for example, by the purification steps described below. Then, the amino acid sequence thereof is determined by the usual method such as Edman degradation, from which the gene sequence of the α-GARE is assumed. Then, based on the gene sequence thus obtained, a DNA fragment, RNA fragment, or the like is produced by the usual method such as chemical synthesis or the like. Then, the genes of the α-GARE of the invention can be obtained by cloning the genes encoding the α-GARE from a novel bacterial strain of the invention using the DNA fragment, RNA fragment, or the like as a primer, probe, or the like.

BEST MODE FOR CARRYING OUT THE INVENTION

Figure 1:
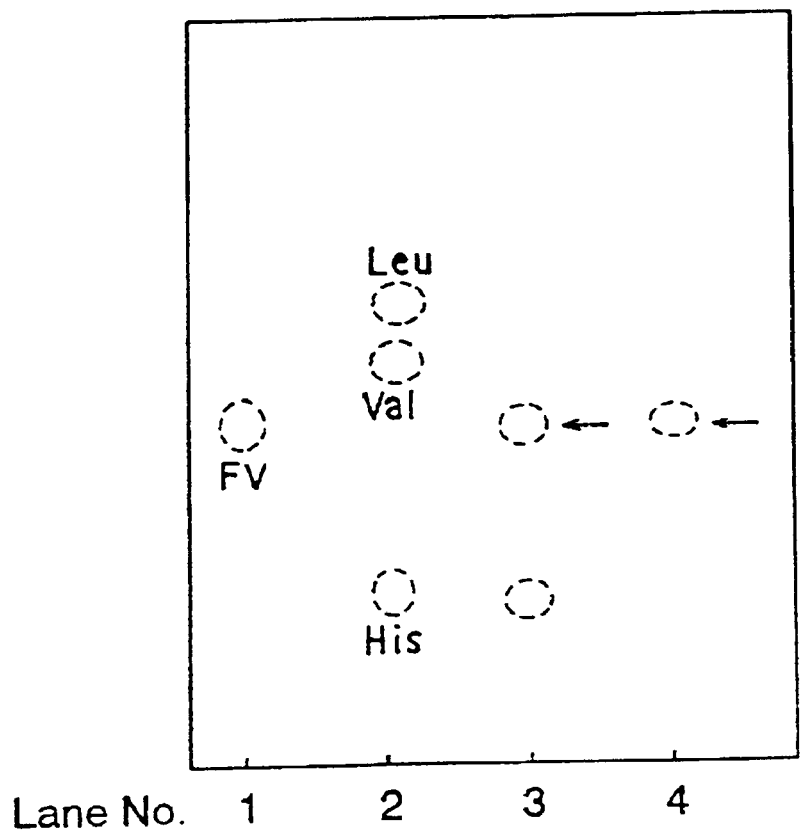
FIG. 1 is a chromatogram resulting from TLC analysis for degradation products obtained by degrading glycated peptides with a culture supernatant of a bacterial strain of the genus Corynebacterium in an example of the present invention.

Screening of a bacterial strain producing α-GARE according to the present invention can be carried out, for example, by culturing the bacterial strain in the soil according to an isolation culture method, inducing a degradation reaction of a glycated peptide by the resultant culture solution, and then analyzing the resultant degradation product by thin layer chromatography (TLC), as specifically described below. The inventors of the present invention have conducted an elaborate study on how to isolate the bacterial strain producing the α-GARE and finally established the following screening method. It can be asserted with good reason that success in isolating the bacterial strain producing the α-GARE of the invention is attributed to the establishment of this screening method.

(1) Culture Method

The liquid nutrient medium shown below is sterilized at 121° C. for 20 minutes in an autoclave. A soil sample is suspended in sterilized water, which is then added to the above-mentioned sterilized liquid nutrient medium, which is then cultured by a shake culture (111 rpm) at 30° C. for 48 hours. The culture solution thus obtained is centrifuged (12,000 G, 15 min, 4° C.) and the supernatant is collected.

| (Liquid Nutrient Medium) | |
|---|---|
| Malt extract | 2.0 g |
| (the trade name "Malt extract", Difco Laboratories) | |
| D-glucose (Nacalai Tesque, Inc.) | 2.0 g |
| Peptone | 0.1 g |
| (the trade name "Becto peptone", Difco Laboratories) | |
| Distilled water | 100 ml |

(2) Degradation Reaction of Glycated Peptide
(Method of Producing Glycated peptide and Glycated Amino Acid)

Using valine, glucose, and each peptide shown below, a glycated peptide with a glycated α-amino group whose amino acid sequence is identical to the N-terminal amino acid sequence of the β-chain of HbA1c and α-fructosyl valine (Hereinafter, referred to as "FV") are produced according to the usual method.
(Peptide)

Val-His (Peptide Institute Inc.: The glycation product thereof hereinafter is referred to as "F2P".)

Val-His-Leu (Peptide Institute Inc.: The glycation product thereof hereinafter is referred to as "F3P".)

Val-His-Leu-Thr (Biolink Corporation: The glycation product thereof hereinafter is referred to as "F4P".)

Val-His-Leu-Thr-Pro (Sigma Chemical Co.: The glycation product thereof hereinafter is referred to as "F5P".)

Val-His-Leu-Thr-Pro-Glu-Glu-Lys-Ser (Biolink Corporation: The glycation product thereof hereinafter is referred to as "F9P".)

(L-Amino acid)

Val, Leu, and His (Wako Pure Chemical Industries, Ltd.)

(Degradation Method)

The above glycated peptides respectively are dissolved in distilled water so as to give a concentration of 0.01 M to prepare glycated peptide solutions. Subsequently, 50 µl of the glycated peptide solutions respectively are mixed with 100 µl of the above culture supernatant, and the resultant mixtures are reacted at 37° C. overnight. The reaction solutions thus obtained are then lyophilized.

(3) TLC analysis

The degradation products of the above glycated peptides are analyzed by TLC for the presence or absence of an α-GARE activity. The reagent to be used and the method of conducting the analysis are described in the following.

(Thin Layer Plate)

Trade name "Pre-Coated TLC plate SILICA GEL 60" (Merck & Co,. Inc.)

(Detection Reagent)

Ninhydrin (Funakoshi Co., Ltd.) is dissolved in 75 vol. % ethanol so as to give a concentration of 0.5 vol. %.

(Development Solvent)

Butanol (Nacalai Tesque, Inc.), an acetic acid (Nacalai Tesque, Inc.), and distilled water are mixed with each other in the volume ratio of 2:1:1.

(Method of Conducting Analysis)

The above thin layer plate previously is prepared so as to have a solvent developing distance of 8 cm and a starting line of a sample spot is set at 1 cm from the bottom of the thin layer plate. Just before starting TLC analysis, the above-mentioned lyophilized reaction solutions respectively are dissolved in 15 µl of 50 vol. % ethanol, which are then spotted on the starting line with a 25 µl syringe. As controls, the above-mentioned FV and respective amino acids also are spotted on the starting line in the same manner. Then, the thin layer plate is placed in a development chamber that previously has been saturated with the above-mentioned developing solvent until the development solvent rises up to a distance of about 8 cm from the starting line. The development solvent should be filled in the development chamber in such a manner that the plate is immersed in the solvent up to distance of about 0.5 cm from the bottom.

After the development, the thin layer plate completely is air-dried in a draft, onto which the above detection reagent (ninhydrin solution) is sprayed. Then, the plate is heated with a preheated hot stirrer (100° C.) to conduct a coloring test. In this coloring test, the sample exhibiting the same mobility as that of the control FV is determined as α-GARE activity positive. The bacterial stain of the culture solution used for preparing the α-GARE-activity-positive sample is the strain producing α-GARE.

The TLC analysis is not limited to the above-mentioned ninhydrin detection and can be, for example, a fluorescence detection using another reagent such as fluorescamine and ethylenediamine sulfate.

Further, as the above controls, α-GA of a glycated protein or glycated peptide serving as a substrate, for example, preferably is used.

Examples of novel bacterial strains isolated by the present inventor with this screening method include *Corynebacterium ureolyticum* KDK1002 (FERM P-17135) and *Pseudomonas alcaligenes* KDK1001 (FERM P-17133).

The substrate usable for the detection of α-GARE according to the present invention and for the determination of an α-GARE activity is not limited to the above-mentioned glycated peptides etc. Examples of the substrate include a glycated protein, glycated peptide, and the like having a glycated N-terminal α-amino group. In the case where such glycated protein, glycated peptide, and the like are used as a substrate, α-GARE can be detected/determined, for example, by causing a redox reaction (e.g., color development reaction) of the released α-GA using the FAOD described later.

Examples of the above glycated protein include HbA1c and glycated globin. These glycated proteins may be those occurring naturally or those synthesized by Amadori rearrangement between sugars and proteins. The glycated globin can be prepared by the globinization of the HbA1c that has been purified using HPLC etc., according to the method proposed by Teale (Teale, F. W. J, Biochem, Biophys, Acta, 35, 543, 1959). When glycating various proteins by synthesis, sugars to be used are not specifically limited. Examples of the sugars include aldose, e.g. glucose, and ketose.

The above glycated peptide can be prepared, for example, by degrading the above-mentioned glycated protein with a protease. Alternatively, the above glycated peptide can be synthesized by the Amadori rearrangement between sugar and a synthetic peptide. The length of the glycated peptides is not specifically limited. However, the number of amino acid residues is in the range of 2 to 20 and preferably in the range of 2 to 8, for example.

As the peptide used in the Amadori rearrangement with sugar, a natural peptide and synthetic peptide can be used, for example. The amino acid composition of these peptides is not specifically limited. However, the peptide containing no arginine or lysine preferably is used. If the peptide containing no arginine or lysine are glycated, only an α-amino group thereof is glycated to give a glycated peptide. Accordingly, by using such glycated peptide, only an α-GARE activity can be detected.

Specifically, in the case where α-GARE is used for the determination of HbA1c, the above glycated peptides preferably have the amino acid sequence that is identical to the N-terminal amino acid sequence of the β-chain of HbA1c. The glycated peptide in which the α-amino group of N-terminal Val is glycated as described in "Degradation Reaction of Glycated Peptide" above is an example of such glycated peptide. Further, by degrading HbA1c with trypsin for example, a glycated peptide with eight amino acid residues in which the α-amino group of the N-terminal Valine is glycated can be obtained.

Further, in the case where the glycated peptide and the like having a glycated N-terminal α-amino group are used as a substrate for the α-GARE, the α-GARE can be detected/determined not only by detecting the released α-GA but also by detecting the remaining peptide after the α-GA has been released.

Such glycated peptide is not specifically limited and can be, for example, dipeptides such as FV-Leu (hereinafter, "FVL"), FV-Gln (hereinafter, "FVQ"), FV-Ala (hereinafter, "FVA"), and FV-Asn (hereinafter, "FVN"). FV is released from these dipeptides by the α-GARE, thereby generating Leu, Gln, Ala, and Asn, respectively. The α-GARE can be detected by reacting Leu with leucine dehydrogenase; Gln with glutamate dehydrogenase; Ala with alanine amine transferase, α-ketoglutaric acid, and lactate dehydrogenase; Ans with asparagine aminotransferase, α-ketoglutaric acid, malate dehydrogenase, etc., and then determining NADH generation or NAD generation by measuring the absorbance (at the wavelength of 340 nm).

Further, examples of a glycated tripeptide include FV-Leu-Ser (hereinafter, "FVLS"). FV is released from FVI5 by α-GARE, thereby generating Leu-Ser. The Leu-Ser is degraded by hydrolase such as aminopeptidase, chymotrypsin, or proteinase K to give leucine, and the leucine thus generated can be determined in the same manner as above. The length of the peptide is not specifically limited.

Further, as a substrate for α-GARE, it is also possible to use a substrate including an amino acid and a detection group, in which the amino acid has a glycated α-amino group; the detection group is bound to an α-carboxyl group of the amino acid by an amide linkage or ester linkage, and the detection group cannot be detected in its binding state whereas it can be detected if released.

α-GARE cleaves the amide linkage or ester linkage between α-GA and the detection group upon reacting with the above-mentioned substrate, thereby releasing the α-GA and the detection group. The detection group released due to this cleavage develops color/fluorescence for example, thus enabling the detection/determination of the α-GARE.

The above detection group is not specifically limited, and a detection group that can be detected by color or fluorescence it develops as described above preferably is used, for example. Examples of the detection group that can be detected by color include paranitroanilide (hereinafter, referred to as "p-NA"), paranitrophenol, indole, β-naphthylamide, and 4-methoxy-β-naphthylamide (4MβNA). Further, examples of the detection group that can be detected by fluorescence include 4methyl-coumaryl-7-amide. Specifically, when p-NA or paranitrophenol is used, the absorbance around the wavelength of 405 to 410 nm, for example, is measured with a spectrophotometer etc. On the other hand, when 4-methyl-coumaryl-7-amide is used, the absorbance around the wavelength of 460 nm, for example, is measured after being excited at the wavelength of 380 nm.

The reason why the α-GARE can release the α-GA regardless of whether the detection group is bound to the α-carboxyl group by the amide linkage or ester linkage is conceived that the α-GARE recognizes the glycated site of the α-amino group to release the α-GA.

The above-mentioned substrate for α-GARE including the detection group bound to the α-carboxyl group can be prepared, for example, using a commercially available amino acid with a detection group bound thereto and a sugar, according to the usual method.

α-GARE of the invention can be produced by culturing an α-GARE-producing bacterial strain of the invention, for example, according to a method equivalent to the above-mentioned culture method. In the case where *Corynebacterium ureolyticum* KDK1002 (FERM P-17135) is used, culture conditions of the strain are, for example, the culture temperature in the range of 20° C. to 37° C., the culture time in the range of 18 to 72 hours, and the culture medium pH in the range of 7.0 to 8.0. On the other hand, in the case where *Pseudomonas alcaligenes* KDK1001 (FERM P-17133) is used, culture conditions of the strain are, for example, the culture temperature in the range of 20° C. to 400° C., the culture time in the range of 18 to 72 hours, and the culture medium pH in the range of 5.0 to 10.0.

Further, by separating and purifying the α-GARE in the culture solution according to the usual method, an enzyme preparation of the α-GARE can be obtained. The purification of the α-GARE can be achieved by combining known methods such as salting-out with ammonium sulfate or the like, isoelectric precipitation, ethanol precipitation, ion-exchange chromatography, gel chromatography, affinity chromatography, hydrophobic chromatography, etc. The following is an example of a method of purifying the α-GARE derived from *Corynebacterium ureolyticum* KDK1002 (FERM P-17135).

First, the above-mentioned culture solution is centrifuged (12,000 G, 15 min, 4° C.) to remove the bacterial cells and the supernatant is obtained. Then, cold ethanol is added to the supernatant so as to give a concentration of 50 vol. %. The resultant solution is stirred sufficiently and left at 4° C. for about 20 minutes. Then, the solution is centrifuged (12,000 G, 15 min, 4° C.) to obtain a supernatant. Again, cold ethanol is added to the supernatant so as to give a concentration of 85 vol. % and the resultant solution is stirred. Subsequently, the solution is left and centrifuged in the same manner as above and the precipitate is collected. The precipitate is then dissolved in purified water.

The solution thus obtained is applied to a column (the trade name "Poros HQ/M" available from PE Biosystem, Inc.) and non-attached fractions are eluted with 10 mM Tris hydrochloric acid (HCl) buffer (pH 7.5) and collected. Then, the non-attached fractions are applied to another column (the trade name "Bio-Scale CHT-I" available from Bio-Rad Laboratories) and non-attached fractions are eluted with 1 mM potassium phosphate buffer (pH 6.0) and collected. In this manner, a partially purified enzyme solution of the α-GARE according to the present invention can be obtained. It is to be noted that α-GAREs derived from other novel bacterial strains of the invention can be purified in the same manner.

Further, the culture medium used for culturing the novel bacterial strains according to the present invention is not limited to the above-mentioned liquid nutrient medium. For example, the hemoglobin (Hb) culture medium show below also can be used. Further, the Hb solution contained in this Hb medium can be prepared in the manner described below.

| (Hb Culture Medium: pH 6.0) | |
|---|---|
| Hb solution | 0.2 wt. % |
| $K_2HPO_4$ | 0.2 wt. % |
| $MgSO_4 \cdot 7H_2O$ | 0.02 wt. % |
| Trace metal salt solution | 1.0 wt. % |
| Trace vitamin solution | 0.2 wt. % |

(Hb Solution)

Fresh blood is centrifuged (2,000 G, 10 min, room temperature) and the red blood cells are collected. The equivalent amount (volume) of distilled water is added to the red blood cells to induce hemolysis. The resultant hemolysate is then centrifuged (2,000 G, 15 min, room temperature) to remove red cell membranes etc. The solution thus obtained is used as the Hb solution.

| (Trace Metal Salt Solution) | |
|---|---|
| $CaCl_2 \cdot 2H_2O$ | 200 mg |
| $H_3BO_3$ | 50 mg |
| $CuSO_4 \cdot 5H_2O$ | 20 mg |
| KI | 50 mg |
| $FeSO_4 \cdot 7H_2O$ | 100 mg |
| $MnSO_4 \cdot 5H_2O$ | 200 mg |
| $ZnSO_4 \cdot 7H_2O$ | 200 mg |
| $Na_2MoO_4 \cdot 2H_2O$ | 50 mg |
| Residue | water (the total volume = 500 ml) |
| (Trace Vitamin Solution) | |
| Ca-pantothenic acid | 40 mg |
| Inositol | 20 mg |

| | |
|---|---|
| Niacin | 40 mg |
| p-aminobenzoate | 20 mg |
| Pyridoxine hydrochloride | 40 mg |
| Thiamine hydrochloride | 40 mg. |
| Biotin | 0.2 mg |
| Vitamin $B_{12}$ | 0.05 mg |
| Residue | water (the total volume = 100 ml) |

Next, a method of determining a glycated protein or a glycated peptide according to the present invention will be explained by taking as an example the case where a sample is blood cells and the glycated protein (e.g., HbA1c) contained therein are determined using α-GARE and FAOD.

First, blood cell fractions are separated from the whole blood according to the usual method such as centrifugal separation and hemolysis of the blood cell fractions is induced. The method of inducing the hemolysis is not specifically limited. Examples of the method include a method using a surfactant, a method using ultrasonic waves, and a method utilizing the difference in osmotic pressure. Among these, the method using a surfactant is preferable on account of the ease of operation.

Examples of the surfactant include polyoxyethylene-p-t-octylphenyl ethers such as, for example, the trade name "Triton X-100"; polyoxyethylene sorbitan alkyl esters such as, for example, the trade name "Tween-20"; and poly(oxyethylene) alkyl ethers such as, for example, the trade name "Brij 35". The treatment with the above surfactant can be carried out under the following conditions: for example, in the case where the solution to be treated contains 1 to 10 vol. % of blood cells, the surfactant is added to the solution so as to give a concentration of 0.1 to 1 wt. % and the resultant mixture is stirred at room temperature for about 5 seconds to 1 minute.

Subsequently, the above-mentioned sample hemolysate is enzyme-treated with the α-GARE of the invention, thereby releasing α-GA from the glycated protein in the sample hemolysate. The above-mentioned enzyme treatment with the α-GARE is conducted, for example, in buffer. The treatment conditions are decided appropriately depending on, for example, the type (e.g., difference in derivation or the like) of the α-GARE to be used and the types and concentration of the glycated protein or glycated peptide.

For example, in the case where the analyte is HbA1c and the α-GARE derived from *Corynebacterium ureolyticum* KDK1002 (FERM P-17135) is used, the enzyme treatment is conducted, for example, under the following conditions: the α-GARE concentration of the reaction solution in the range of 0.01 U/l to 1 KU/1, the temperature in the range of 15° C. to 60° C., the reaction time in the range of 3 minutes to 6 hours, and the pH in the range of 5.0 to 10.0; preferably, the temperature in the range of 30° C. to 37° C., the reaction time in the range of 5 to 60 minutes, and the pH in the range of 6 to 8. In this case, Tris HCl buffer, phosphate buffer, Good's buffer (EPPS buffer, PIPES buffer, etc.), and the like can be used as the above buffer. Also, α-GARE derived from other novel bacterial strains of the invention can be used in the same manner.

Next, the degradation product (α-GA) obtained through the above-mentioned α-GARE treatment is treated with FAOD. The degradation reaction of the α-GA catalyzed by FAOD is represented by Formula (1) below.

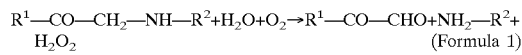

(Formula 1)

As shown in Formula (1), if the degradation product (α-GA: $R^1$—CO—$CH_2$—NH—$R^2$) obtained through the α-GARE treatment is treated with FAOD, a sugar ($R^1$—CO—CHO), an amino acid ($NH_2$—$R^2$), and hydrogen peroxide ($H_2O_2$) are generated.

In Formula (1), $R^1$ denotes a residue derided from a sugar that is not yet subjected to the glycation reaction (i.e., sugar moiety). The sugar moiety ($R^1$) is an aldose residue when the unreacted sugar is aldose, and a ketose residue when the unreacted sugar is ketose. When the unreacted sugar is glucose, for example, the sugar in the glycated product takes on the fructose structure after the glycation reaction due to Amadori rearrangement. In this case, the sugar moiety ($R^1$) is a glucose residue (aldose residue). This sugar moiety ($R^1$) can be represented, for example, by —$[CH(OH)]_n$—$CH_2OH$ where n denotes an integer of 0 to 6.

Further, in Formula (1), $R^2$ denotes an amino acid residue having a glycated α-amino group and can be represented by Formula (2) below. In Formula (2), $R^3$ denotes an amino-acid side chain group.

(Formula 2)

The above FAOD is not specifically limited as long as it catalyzes the above-mentioned degradation reaction and may have other catalytic functions, for example. Similarly to the enzyme treatment with α-GARE, the FAOD treatment preferably is conducted in buffer. The buffer is not specifically limited and can be, for example, Tris HCl buffer, EPPS buffer, PIPES buffer, etc.

The FAOD treatment is conducted, for example, under the following conditions: the FAOD concentration in the reaction solution in the range of 0.1 to 10 KU/l, the temperature in the range of 15° C. to 50° C., the reaction time in the range of 1 to 60 minutes, and the pH in the range of 6 to 9; preferably, the FAOD concentration in the range of 0.5 to 2 KU/l, the temperature in the range of 30° C. to 37° C., the reaction time in the range of 5 to 20 minutes, and the pH in the range of 7 to 8.

Next, the hydrogen peroxide generated by the FAOD treatment is determined utilizing a redox reaction, by using the peroxidase (POD) and substrate that develops color by oxidization.

Generally, the redox reaction is induced in buffer under the conditions decided appropriately depending on the concentration of the hydrogen peroxide in the reaction solution, etc. For example, the redox reaction is induced under the following conditions: the POD concentration in the reaction solution in the range of 10 U/l to 400 KU/l, the reaction temperature in the range of 15° C. to 40° C., the reaction time in the range of 0.1 to 5 minutes, and the pH in the range of 5 to 10; more preferably, the POD concentration in the range of 50 U/l to 20 KU/l, the reaction temperature in the range of 30° C. to 37° C., the reaction time in the range of 0.1 to 1 minutes, and the pH in the range of 5 to 8. Furthermore, the buffer is not specifically limited and can be, for example, the same buffer as that used in the above-mentioned FAOD treatment.

In the case where the chromogenic substrate described above is used as the substrate, the concentration of the hydrogen peroxide can be determined by measuring the color development (i.e., absorbance of the reaction solution) with a spectrophotometer. From the concentration of the hydrogen peroxide, the concentration of the glycated protein in the sample can be determined.

In this determination process, the respective treatment steps may be performed individually as described above. In some cases, some of the steps or all of the steps may be performed simultaneously. For example, the α-GARE treatment step and the FAOD treatment step can be performed simultaneously by adding the α-GARE and FAOD to the sample at the same time to cause the reaction. Also, the FAOD treatment step and the color development step using POD can be performed simultaneously by adding FAOD, POD, and the chromogenic substrate to the degradation product obtained through the α-GARE treatment at the same time to cause the reaction. In addition, the step of inducing hemolysis by the surfactant and the α-GARE treatment step also can be perform simultaneously.

EXAMPLES

Example 1

In the present example, a glycated peptides having α-GA were reacted with a culture supernatant of a novel bacterial strain producing α-GARE according to the present invention to release the α-GA therefrom. Unless otherwise described, culture of the bacterial strain, degradation of the glycated peptides, and TLC analysis of the degradation products were conducted in the same manner as in the above-mentioned screening method.

First, *Corynebacterium ureolyticum* KDK1002 (FERM P-17135) was inoculated into 200 ml of the above-mentioned liquid nutrient medium, and then was cultured by a shake culture at 30 °C. for 48 hours. The culture solution thus obtained was centrifuged to remove the bacterial cells and the supernatant obtained was used as a crude enzyme solution.

Figure 2:
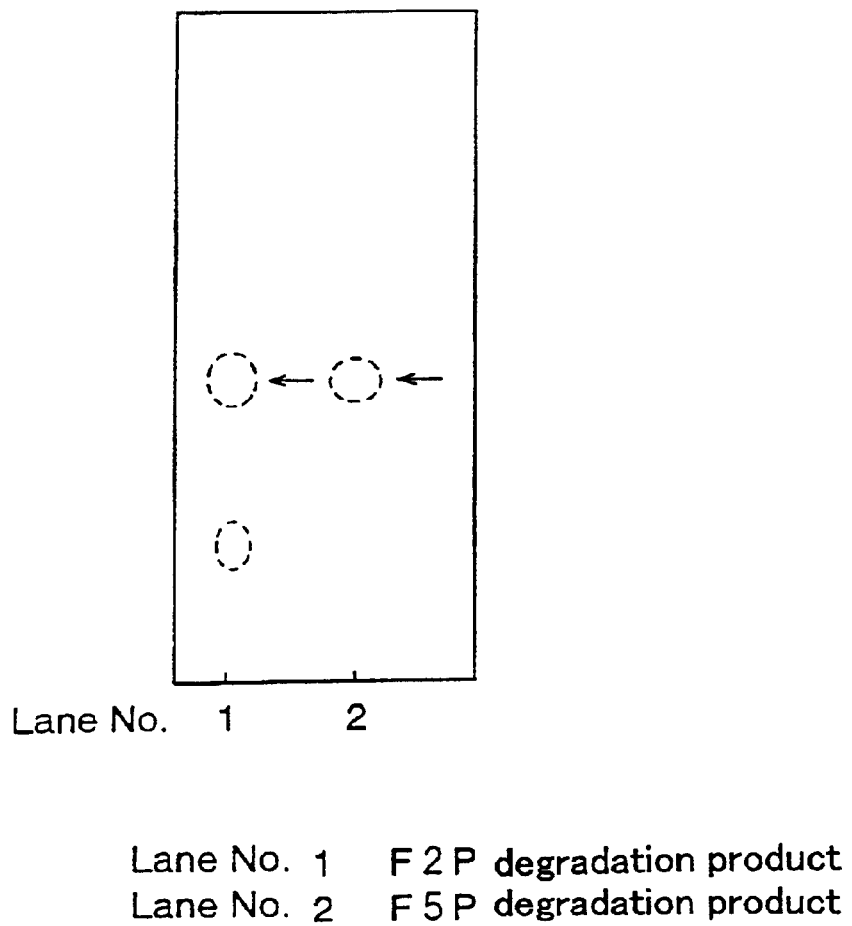
FIG. 2 is another chromatogram resulting from TLC analysis for degradation products obtained by degrading glycated peptides with a culture supernatant of a bacterial strain of the genus Corynebacterium in the same example.

Next, 50 μl of the above-mentioned 0.01 M solutions of the glycated peptides (F2P, F3P, and F5P) respectively were mixed with 100 μl of this crude enzyme solution. The resultant mixtures were reacted at 37° C. overnight, and the reaction solutions thus obtained were analyzed by TLC. The results of this TLC analysis are shown in FIGS. 1 and 2. In FIG. 1, Lane No. 1 shows a control (FV), Lane No. 2 shows other controls (Leu, Val, His), Lane No. 3 shows the F2P degradation product, and Lane No. 4 shows the F3P degradation product. In FIG. 2, Lane No. 1 shows the F2P degradation product and Lane No. 2 shows the F5P degradation product. Further, mobility of the spots marked with the arrows in these drawings are shown in Table 1 below.

Example 2

Figure 3:
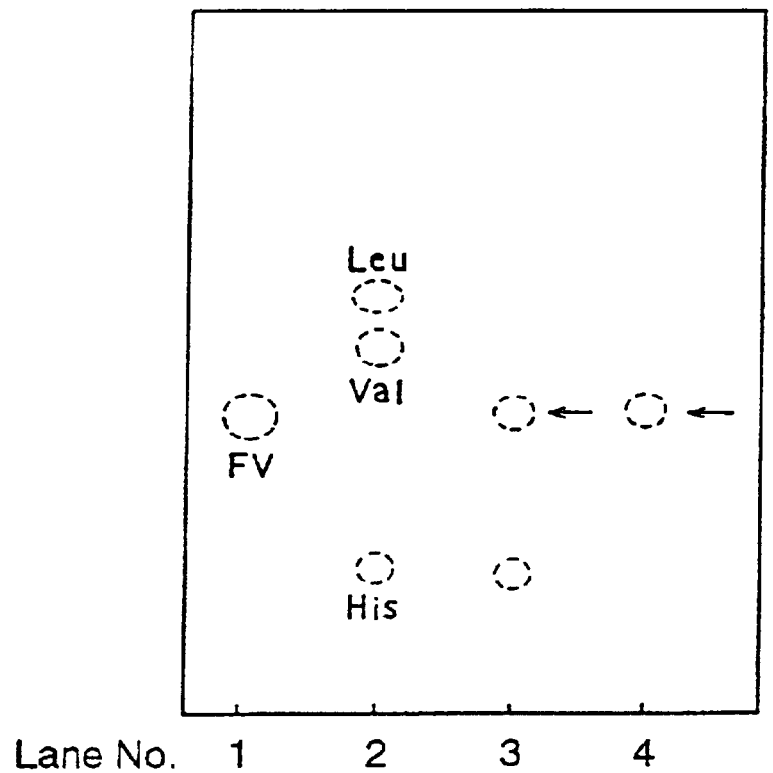
FIG. 3 is a chromatogram resulting from TLC analysis for degradation products obtained by degrading glycated peptides with a culture supernatant of a bacterial strain of the genus Pseudomonas in another example of the present invention.

*Pseudomonas alcaligenes* KDK1001 (FERM P-17133) was inoculated into the liquid nutrient medium. Then, according to the same manner as in Example 1, culture of the bacterial strain, degradation of the glycated peptides, and TLC analysis of the degradation products were conducted. The results of this TLC analysis are shown in FIG. 3. In FIG. 3, Lane No. 1 shows a control (FV), lane No. 2 shows other controls (Leu, Val, His), Lane No. 3 shows the F2P degradation product, and Lane No. 4 shows the F3P degradation product. Further, mobility of the spots marked with the arrows in FIG. 3 also are shown in Table 1 below.

TABLE 1

| FIG. No. | Samples | Mobility |
|---|---|---|
| FIG. 1 | Control FV | 0.43 |
|  | F2P degradation product | 0.43 |
|  | F3P degradation product | 0.43 |
| FIG. 2 | F2P degradation product | 0.44 |
|  | F5P degradation product | 0.44 |
| FIG. 3 | Control FV | 0.46 |
|  | F2P degradation product | 0.46 |
|  | F3P degradation product | 0.46 |

As shown in FIGS. 1, 2, and 3 and Table 1 above, the degradation products of the glycated peptides treated with the respective crude enzyme solutions were seen as the spots (marked with the arrows in the drawings) with the same mobility as that of the spot of the control FV. Also, the F5P degradation product in Example 2 was seen as the spot (mobility 0.46: not shown in the drawing) with the same mobility as that of the spot of the control FV. These results demonstrate that α-GARE according to the present invention releases α-GA from a glycated peptide. Further, since the spots of the above degradation products had the different mobility than that of Val, it was found that the sugar was not dissociated from FV released by the α-GARE. In addition, as shown in FIGS. 1, 2, and 3, the F2P degradation product exhibited the spots of FV and His. The reason why the F3P degradation product and F5P degradation product did not exhibit the spots of degradation products other than FV (dipeptide and tetrapeptide) is considered that they are hardly detect by this TLC method.

Example 3

In the present example, release of α-GA (FV) was confirmed in a glycated peptide that had been treated with a crude enzyme derived from a novel bacterial strain according to the present invention.

*Corynebacterium ureolyticum* KDK1002 (FERM P-17135) was cultured in the above-mentioned Hb culture medium (pH 6.0) at 28° C. for 5 days. Then, the resultant culture solution was centrifuged (12,000 G, 15 min, 4° C.), and the supernatant obtained was used as a crude enzyme solution.

The crude enzyme solution and 50 μl of 0.01 M F4P solution were mixed with each other and the resultant mixture was reacted at 37 °C. overnight. The reaction solution thus obtained was applied to an ultrafiltration membrane (5 kDa molecular weight cut off: Millipore Corporation) to remove high molecular substances such as proteins or the like. The solution thus obtained was then lyophilized.

Next, the lyophilized product was dissolved in 20 μl of the eluent A shown below. The resultant solution was subjected to reverse phase chromatography under the conditions shown below and the solution was fractionated every 15 seconds (250 μl/1 fraction) after the start of the analysis. Further, FV as a control was eluted under the same conditions and the elution time thereof was measured.

| (Reverse Phase Chromatography) | |
|---|---|
| Column; | Trade name "Hypercard" (GL Sciences Inc.) |
| Size; | 100 mm × 4.6 mm |
| Loop; | 1000 μl |
| Eluent A; | trifluoroacetic acid:distilled water = 0.1:100 (volume ratio) |
| Eluent B; | acetone:distilled water:trifluoroacetic acid = 80:20:0.1 (volume ratio) |
| Gradient conditions; | 0 to 25 minutes: 0 to 20 vol. % eluent B after 25 minutes: 20 vol. % eluent B |
| Flow rate; | 1 ml/min |
| Column temperature; | 37° C. |
| Detection wavelength; | 210 nm, 230 nm |

Subsequently, with respect to each separation fraction obtained through the above-mentioned reverse phase chromatography, detection of FV was conducted in the manner described below.

(Detection Method for FV)

First, 20 μl of a hydrogen peroxide aqueous solution was added to 20 μl of the respective separation fraction solutions. Then, 60 μl of the redox solution A shown below was further added and the resultant mixtures were reacted at 37° C. Next, the absorbance of these reaction solutions at the main wavelength of 694 nm and the sub-wavelength of 884 nm was measured by means of a biochemical automatic analysis apparatus (the trade name "JCA-BM 8" available from Japan Electron Optics Laboratory Co. Ltd., hereinafter the same).

| (Composition of Redox Solution A) | |
|---|---|
| Trade name "DA 64" (Wako Pure Chemical Industries, Ltd., hereinafter the same) | 20 µmol/l |
| POD (Type III: Toyobo Co., Ltd., hereafter the same) | 20 KU/l |
| FAOD (Asahi Chemical Industry Co., Ltd.) | 0.5 KU/l |
| Potassuim phosphate buffer (pH 8.0) | 0.1 mol/l |

As a result, color development was observed in the separation fractions corresponding to the elution time of 5 to 6 minutes in the reverse phase chromatography. Such elution time was equivalent to that of the control FV and thus suggested that FV was present in the F4P degradation product.

Figure 4:
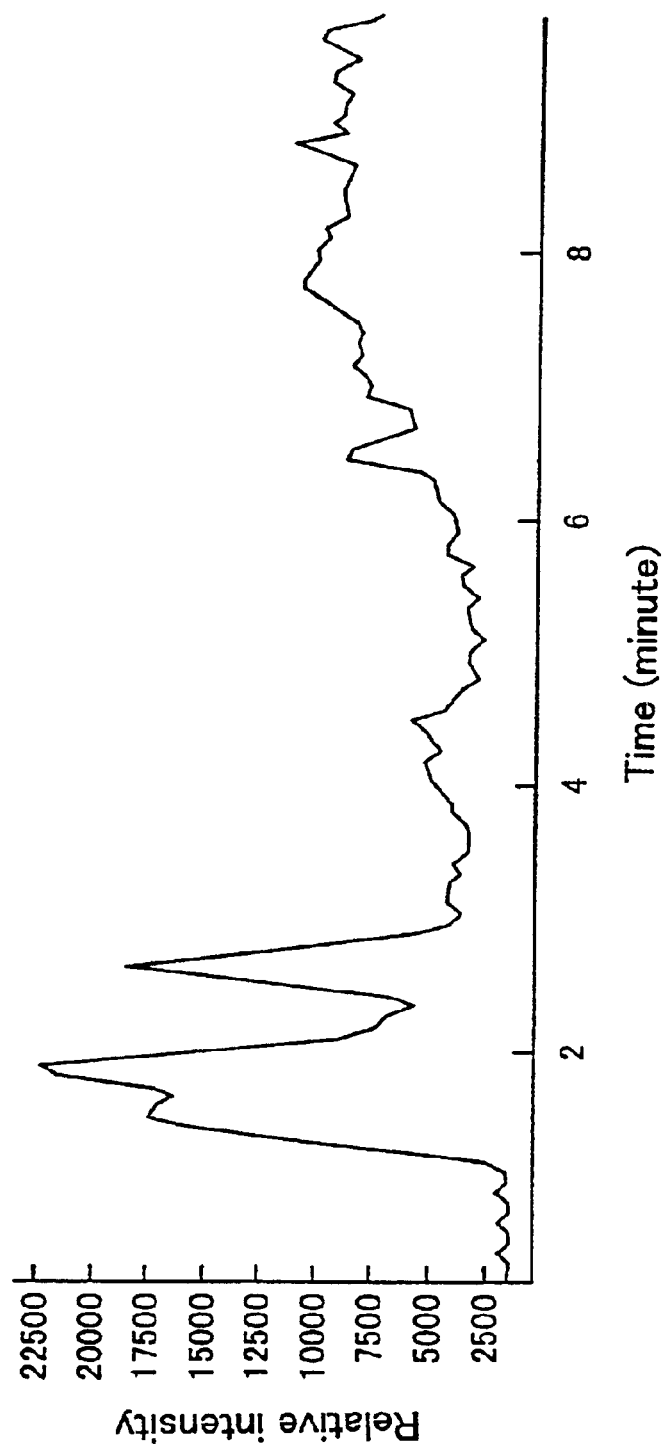
FIG. 4 is a total ion chromatogram resulting from LC-MS analysis for a degradation product obtained by degrading a glycated peptide with a culture supernatant of a bacterial strain of the genus Corynebacterium in still another example of the present invention.
Figure 5:
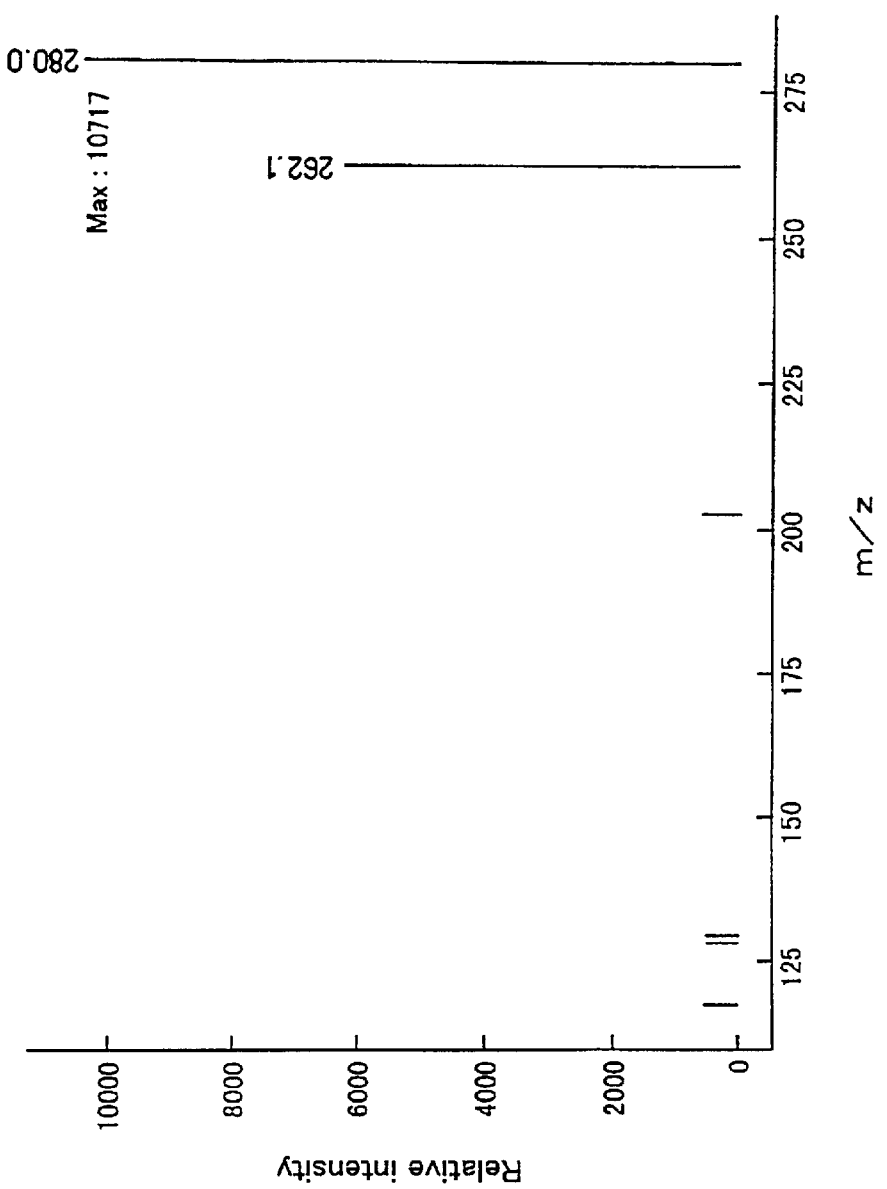
FIG. 5 is an MS spectrum resulting from LC-MS analysis for a degradation product obtained by degrading a glycated peptide with a culture supernatant of a bacterial strain of the genus Corynebacterium in the same example.

Next, with respect to the separation fractions in which color development was observed, liquid phase chromatography (LC)/mass spectrum (MS) analysis was conducted under the conditions shown below. The results are shown in FIGS. 4 and 5. FIG. 4 is a total ion chromatogram and FIG. 5 is a MS spectrum of the eluted product at the elution time of 1.84 minute.

| (LC conditions) | |
|---|---|
| Column; | Trade name "Inertsil ODS 3" (GL Sciences Inc.) |
| Size; | length = 150 mm, inside diameter = 2.1 mm particle size of ODS carrier = 5 µm |
| Eluent; | acetonitrile:0.1 vol. % formic acid aqueous solution = 10:90 (volume ratio) |
| Flow rate; | 0.2 ml/min |
| Column temperature; | 40° C. |
| (MS conditions) | |
| Model; | Trade name "LC1100MSD" (Agilent Technologies, Inc.) |
| Mass range; | 100 to 500 am |
| Ionization; | |
| Nebulizer: | $N_2$ |
| Drying gas: | $N_2$ (10 l/min, 350° C.) |
| Applied voltage: | 60 V |

As a result, three peaks were detected as shown in FIGS. 4 and 5. More specifically, at the elution time of 1.84 minute, the peak at mass number 280, which is the mass number of FV, and the peak at mass number 261, which is the quasi-molecular peak of FV, were detected. Since the largest peak in the mass spectrum was the peak at mass number 280, which indicates FV, it was confirmed that F4P had been degraded to generate FV.

Example 4

In the present example, an α-GARE activity was confirmed at various α-GARE concentrations.
(1) Preparation of Partially Purified Enzyme

*Corynebacterium ureolyticum* KDK1002 (FERM P-17135) and *Pseudomonas alcaligenes* KDK1001 (FERM P-17133) were cultured in the same manner as in Example 3. Supernatants were collected from the respective culture solutions and were used as crude enzyme solutions. Then, 50 ml of the respective crude enzyme solutions were concentrated using the ultrafiltration membrane of 5 kDa molecular weight cut off (the trade name "Ultra Free MC Filter" available from Millipore Corporation), and then were partially purified by gel chromatography conducted under the following conditions.

| (Gel Column Chromatography) | |
|---|---|
| Column: | Trade name "HiLoad 26/60 Superdex 200 pg" (Bio-Rad Laboratories) |
| Column size: | inside diameter = 260 mm, length = 600 mm |
| Flow rate; | 5.2 ml/min |
| Detection wavelength; | 280 nm, 230 nm |
| Eluent: | 20 mM potassium phosphate buffer (pH 7.5) |
| 1 fraction: | 7 ml |

(2) Determination of α-GARE activity

Figure 6:
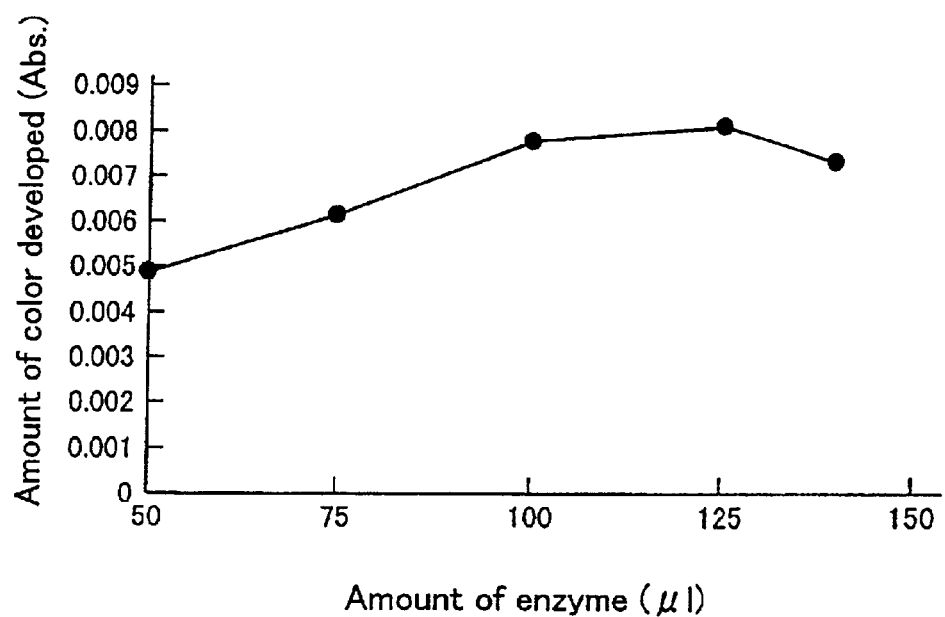
FIG. 6 is a graph showing the relationship between the amount of α-GARE derived from a bacterial strain of the genus Corynebacterium and the absorbance in still another example of the present invention.
Figure 7:
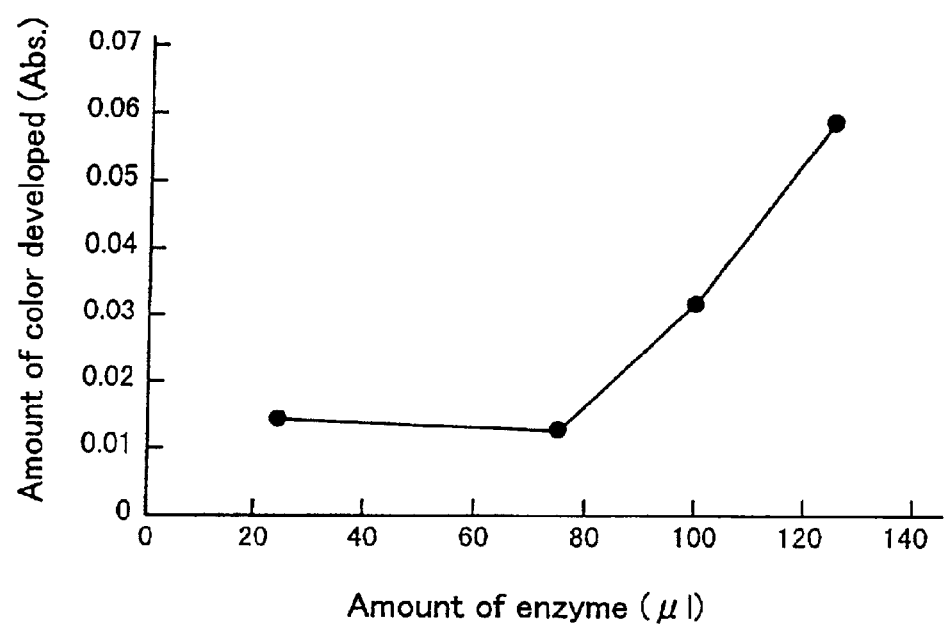
FIG. 7 is a graph showing the relationship between the amount of α-GARE derived from a bacterial strain of the genus Pseudomonas and the absorbance in still another example of the present invention.

The HbA1c digest solution shown below was used as a substrate for the α-GARE derived from *Corynebacterium ureolyticum* KDK1002 (FERM P-17135), and 10 mM F3P (50 mmol/l potassium phosphate buffer: pH 8.0) was used as a substrate for the α-GARE derived from *Pseudomonas alcaligenes* KDK1001 (FERM P-17133). Predetermined amounts (25, 50, 75, 100, 125, and 140 µl) of the respective partially purified α-GAREs were added to 50 µl of the corresponding substrates, respectively. The resultant mixtures were reacted at 37° C. overnight. Subsequently, according to the same manner as in Example 3, a redox reaction was induced in 20 µl of the respective reaction solutions by the use of FAOD and the absorbance of each solution was measured. Then, using the value obtained in the absence of each α-GARE as a blank, an increase in the absorbance per 5 minutes was determined as an α-GARE activity. The results are shown in FIGS. 6 and 7. FIG. 6 is a graph showing the relationship between the amount of the α-GARE derived from *Corynebacterium ureolyticum* KDK1002 (FERM P-17135) and the amount of the color developed (absorbance), and FIG. 7 is a graph showing the relationship between the amount of the α-GARE derived from *Pseudomonas alcaligenes* KDK1001 (FERM P-17133) and the amount of the color developed (absorbance).
(HbA1c Digest Solution)

Human whole blood was washed with a physiological salt solution (0.85 wt. % NaCl) and the blood cells were collected. To the blood cells was added ten times their volume of purified water to hemolyze the blood cells completely. The resultant mixture was centrifuged (10,000 G, 30 min) to separate the blood cell membranes and a hemolysate was thus obtained. Then, 7.5 mg by a Hb amount of the hemolysate at a time was separated according to the method proposed by Bisse and Wieland (J. Chromatogr, (1988), Vol 434, p95–110, Bisse & Wieland) using the trade name "Poly CAT Column" (PolyLC Inc.) of 0.94×20 cm to collect HbA1c. Subsequently, 20 ml of the HbA1c thus collected (hemoglobin concentration of 17 g/l) and 5 ml of 0.2 M sodium acetate buffer (pH 3.0) were mixed with each other. After the pH of the mixture was adjusted to 3.0 by adding acetic acid, 0.35 mg of pepsin (Sigma Chemical Co.) was further added. The resultant solution was incubated at 28° C. overnight. Then, using an ultrafiltration membrane (the trade name "Ultra Free MC Filter" available from Millipore Corporation), high molecular substances such as pepsin or the like were removed. The solution thus obtained was used as an HbA1c digest solution.

As shown in FIG. 6, the activity of the α-GARE derived from *Corynebacterium ureolyticum* KDK1002 (FERM P-17135) increased in an amount-dependent manner when the amount of the α-GARE is in the range of about 50 to 100 μl. On the other hand, as shown in FIG. 7, the activity of the α-GARE derived from *Pseudomonas alcaligenes* KDK1001 (FERM P-17133) increased linearly when not less than about 70 μl of the α-GARE was added.

Example 5

In the present example, thermal stability of α-GARE according to the present invention was confirmed.

Figure 8:
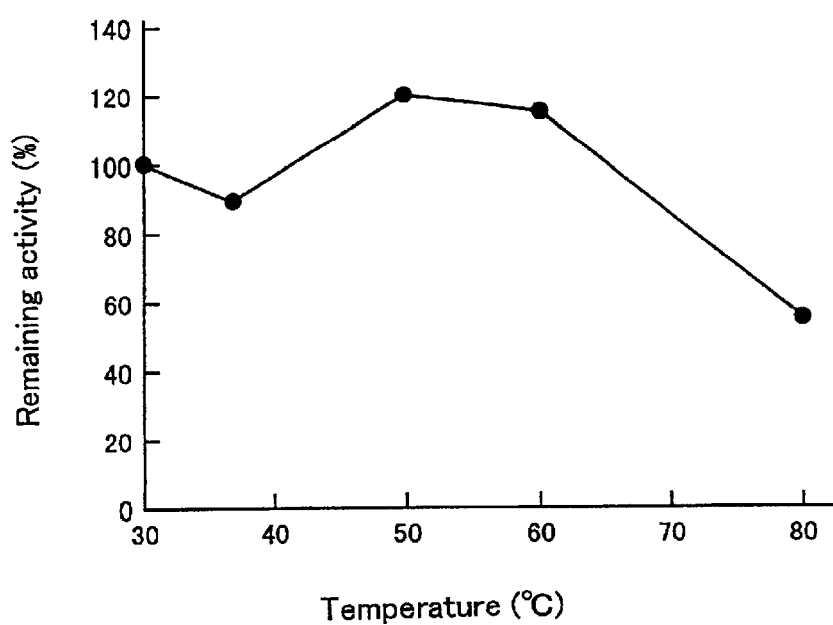
FIG. 8 is a graph showing thermal stability of α-GARE derived from a bacterial strain of the genus Corynebacterium in still another example of the present invention.
Figure 9:
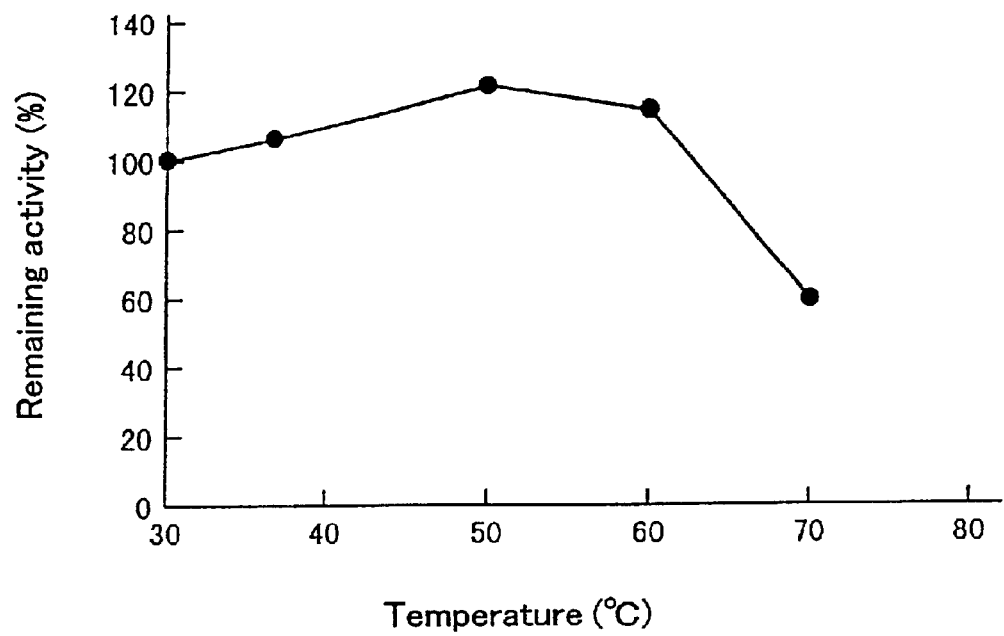
FIG. 9 is a graph showing thermal stability of α-GARE derived from a bacterial strain of the genus Pseudomonas in still another example of the present invention.

According to the same manner as in Example 4, partially purified enzymes were prepared from the α-GARE derived from *Corynebacterium ureolyticum* KDK1002 (FERM P-17135) and the α-GARE derived from *Pseudomonas alcaligenes* KDK1001 (FERM P-17133). The partially purified enzymes were incubated at respective temperatures (30° C., 37° C., 50° C., 60° C., 70° C., and 80° C.) for 15 minutes. Subsequently, 100 μl of the heat-treated partially purified enzymes were mixed with 50 μl of substrates, and the resultant mixtures were reacted at 37° C. overnight. As the substrates for the respective α-GAREs, the same substrates as those used in Example 4 were used. Subsequently, according to the same manner as in Example 3, a redox reaction was induced in 20 μl of the resultant reaction solutions by the use of FAOD and the absorbance of each solution was measured. An increase in the absorbance per 5 minutes was determined as an α-GARE activity and, letting the activity of the non-heat-treated α-GARE be 100%, a remaining activity (%) was calculated. The results are shown in FIGS. 8 and 9. FIG. 8 is a graph showing the thermal stability of the α-GARE derived from *Corynebacterium ureolyticum* KDK1002 (FERM P-17135), and FIG. 9 is a graph showing the thermal stability of the α-GARE derived from *Pseudomonas alcaligenes* KDK1001 (FERM P-17133).

As shown in FIG. 8, the α-GARE derived from *Corynebacterium ureolyticum* KDK1002 (FERM P-17135) remained 100% active even after the heat treatment at 30° C. to 60° C. However, the remaining activity was reduced to about 50% by the heat treatment at 80° C. On the other hand, as shown in FIG. 9, the α-GARE derived from *Pseudomonas alcaligenes* KDK1001 (FERM P-17133) exhibited a remaining activity of 100% even after the heat treatment at 30° C. to 60° C. However, the remaining activity was reduced to about 60% by the heat treatment at 70° C.

Example 6

In the present example, an optimum temperature of α-GARE according to the present invention was confirmed.

Figure 10:
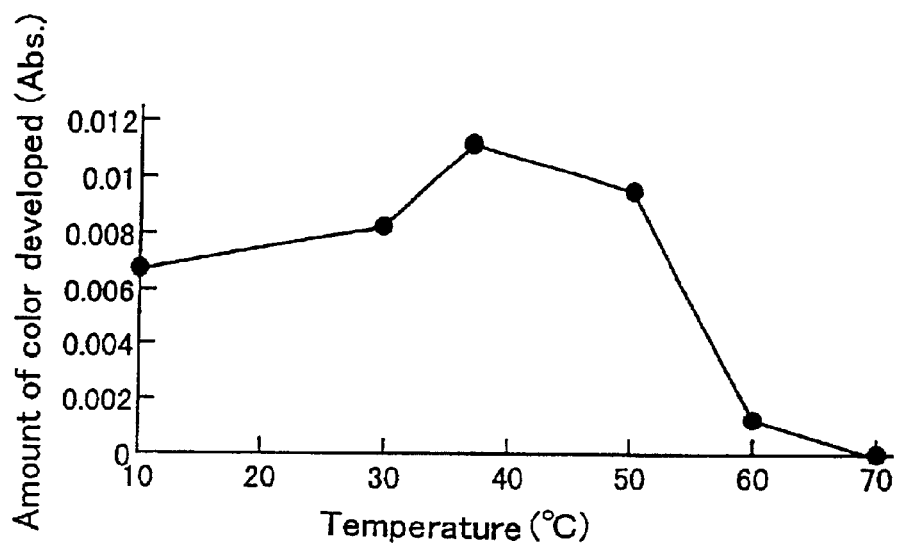
FIG. 10 is a graph showing an optimum temperature of α-GARE derived from a bacterial strain of the genus Corynebacterium in still another example of the present invention.

According to the same manner as that described in Example 4, a partially purified enzyme was prepared from the α-GARE derived from *Corynebacterium ureolyticum* KDK1002 (FERM P-17135). Then, 100 μl of the partially purified enzyme was added to a mixture of 90 μl of the same HbA1c digest solution as that used in Example 5 and 10 μl of potassium phosphate buffer (pH 8.0). The resultant solution was reacted at respective temperatures (10° C., 30° C., 37° C., 50° C., 60° C., and 70° C.) overnight. Subsequently, according to the same manner as in Example 3, a redox reaction was induced in 20 μl of the resultant reaction solutions by the use of FAOD and the absorbance of each solution was measured. Then, an increase in the absorbance per 5 minutes was determined as an α-GARE activity. The result is shown in FIG. 10. FIG. 10 is a graph showing an optimum temperature of the α-GARE derived from *Corynebacterium ureolyticum* KDK1002 (FERM P-17135).

As shown in FIG. 10, the optimum temperature of the α-GARE derived from *Corynebacterium ureolyticum* KDK1002 (FERM P-17135) was about 40° C. to 50° C.

Example 7

In the present example, a molecular weigh of α-GARE according to the present invention was confirmed.

According to the same manner as in Example 3, *Corynebacterium ureolyticum* KDK1002 (FERM P-17135) and *Pseudomonas alcaligenes* KDK1001 (FERM P-17133) were cultured and supernatants were collected from the respective culture solutions. The supernatants were used as crude enzyme solutions. The crude enzyme solutions were separated through gel chromatography conducted under the same conditions as in Example 4. Then, 150 μl of each fraction was added to the mixture of 50 μl of a substrate and 50 mM potassium phosphate buffer (pH 8.0), and the resultant mixture was reacted at 37° C. overnight. As the substrates for the respective α-GAREs, the same substrates as those used in Example 4 were used. Subsequently, according to the same manner as in Example 3, a redox reaction was induced in 20 μl of the resultant reaction solutions by the use of FAOD and the absorbance of each solution was measured. Then, an increase in the absorbance per 5 minutes was determined as an α-GARE activity. The trade name "MW Marker (HPLC)" (Oriental Yeast Co., Ltd.) was used as a molecular weight marker.

As a result, in both the crude enzyme solutions, an α-GARE activity was detected in the fractions corresponding to the molecular weight of about 40,000 to 50,000. Accordingly, it can be assumed that the molecular weight of both the α-GARE derived from *Corynebacterium ureolyticum* KDK1002 (FERM P-17135) and the α-GARE derived from *Pseudomonas alcaligenes* KDK1001 (FERM P-17133) was about 40,000 to 60,000.

Example 8 and Comparative Example 1

In Example 8, glycated peptides were treated with the same α-GARE crude enzyme solutions as those used in Examples 1 and 2, and α-GARE activities of these crude enzyme solutions were measured by causing a redox reaction in the resultant products by the use of FAOD etc. The reagent used in the present example, the composition of the reagent, and the method of determining the α-GARE activities will be described in the following.

(50 mM Glycated Peptide Solution)

The above-mentioned F2P was dissolved in distilled water so as to give a concentration of 50 mM.

| (Buffer A) | |
|---|---|
| 80 mM Tris HCl buffer (pH 8.0) | |
| (Composition of Redox Solution B) | |
| Trade name "DA 64" | 0.1 mmol/l |
| POD | 50 KU/l |
| FAOD (Kikkoman Corporation) | 10 KU/l |
| Buffered A | 80 mmol/l |

First, 490 μl of the crude enzyme solutions prepared in the same manner as in Examples 1 and 2 respectively were mixed with 10 μl of the glycated peptide solution, and the resultant mixtures were reacted at 30° C. overnight to degrade the glycated peptide. To 25 μl of the resultant degradation solutions was added 55 μl of the buffer A and then, 20 μl of the reaction solution B was further added to cause a reaction. Subsequently, the absorbance of each reaction solution at the main wavelength of 694 nm and the sub-wavelength of 884 nm was measured using a biochemical automatic analysis apparatus (the trade name "JCA-BM 8" available from Japan Electron Optics Laboratory Co. Ltd.). Then, α-GARE activities were determined based on the absorbance thus measured and the calibration curve that previously had been prepared by causing a reaction of FV as a reference material by the use of FAOD. The results are shown in Table 2 below. On the other hand, in Comparative Example 1, α-GARE activities were determined in the same manner except that enzyme solutions obtained by dissolving trypsin (Sigma Chemical Co.), papain (Sigma Chemical Co.), and aminopeptidase (Sigma Chemical Co.) in purified water, respectively, to give a concentration of 1 g/l were used in place of the crude enzyme solutions used in Example 8.

TABLE 2

| Bacterial strain | α-GARE activity (U/l) |
|---|---|
| Corynebacterium ureolyticum KDK1002 | 1.43 |
| Pseudomonas alcaligenes KDK1001 | 0.26 |

As shown in Table 2, α-GARE activities were detected in the case where the crude enzyme solution derived from the above two types of novel bacterial strains were used. However, α-GARE activities were not detected in Comparative Example 1 employing the enzyme solutions using trypsin, papain, and aminopeptidase, respectively.

Example 9

In the present example, a glycated peptide was treated with an α-GARE enzyme solution derived from *Corynebacterium ureolyticum* KDK1002, and an α-GARE activity of this enzyme solution was measured by causing a redox reaction in the resultant product by the use of FAOD. The reagent used in the present example, the composition of the reagent, and the method of determining the α-GARE activity will be described in the following.

(Method of Preparing α-GARE Enzyme Solution)

*Corynebacterium ureolyticum* KDK1002 (FERM P-17135) was inoculated into 200 ml of the above-mentioned liquid nutrient medium, and then was cultured by a shake culture method at 30° C. for 48 hours. The culture solution thus obtained was centrifuged to remove bacterial cells and the supernatant was collected. Subsequently, the supernatant was applied to a column (the trade name "Poros HQ/M" available from PE Biosystem, Inc.) and then to another column (the trade name "Bio Scale CHT-I" available from Bio-Rad Laboratories) in the same manner as that described above, to partially purify the α-GARE. Active fractions obtained were used as an α-GARE enzyme solution.

(Method of Preparing Glycated Globin)

According to the method proposed by Teale described above, globin was purified from human blood cells. Then, glucose was added to the globin so as to give a concentration of 10 wt. %. The resultant mixture was left at 40° C. for a week to prepare glycated globin.

The glycated globin was dissolved in distilled water so as to give a concentration of 2 g/l to prepare a glycated globin solution. Then, 100 μl of the α-GARE enzyme solution, 50 μl of the glycated globin solution, and 350 μl of 100 mM Tris HCl buffer (pH 8.0) were mixed with each other, and the resultant mixture was reacted at 37° C. for 3 hours to degrade the glycated globin. Then, using this degradation solution, an α-GARE activity was determined according to the same manner as in Example 8. It is to be noted here that the FAOD (Kikkoman Corporation) specifically acts on an α-GA and thus can determined the α-GARE activity only even when the α-GARE derived from *Corynebacterium ureolyticum* KDK1002 (FERM P-17135) releases not only α-GA but also, for example, an amino acid residue having a glycated ε-amino group. As a result, it was found that the α-GARE activity was 2.1 U/l.

Example 10

In the present example, an α-GARE activity was determined using FV-pNA as a substrate.

According to the same manner as in Example 1, a crude enzyme solution derived from *Corynebacterium ureolyticum* KDK1002 (FERM P-17135) was prepared. Then, 400 μd of the crude enzyme solution was mixed with 100 μl of the reaction reagent C shown below, and the resultant mixture was reacted at 37° C. Color development of pNA released by the α-GARE was measured as the change in absorbance at the wavelength of 410 nm. Then, the change in absorbance per minute was found as an α-GARE activity. The result is shown in Table 3 below.

(Preparation of FV-pNA)

FV-pNA was prepared from Val-pNA (Sigma Chemical Co.) and glucose according to the usual method.

| (Reaction Reagent C) | |
|---|---|
| FV-pNA | 1 ml |
| 50 mM potassium phosphate buffer (pH 8.0) | 20 mol |

TABLE 3

| Sample | α-GARE activity (increase in absorbance per minute) |
|---|---|
| Example 1 | 0.0030 |
| Control | 0.0005 |

As shown in Table 3, an activity of the α-GARE according to the preset invention also can be determined using the amino acid substrate that includes an amino acid having a glycated α-amino group and a detection group bound to an α-carboxyl group by an amide linkage.

As specifically described above, α-GARE according to the preset invention enables the accurate determination of a glycated protein and glycated peptide because it can release α-GA from the glycated protein and glycated peptide so that FAOD easily acts thereon.

Industrial Applicability

As specifically described above, a novel enzyme, α-GARE, according to the present invention can release an amino acid residue having a glycated α-amino group from a glycated protein etc. Accordingly, if α-GARE is used in a method of determining the glycated protein etc. using FAOD, HbA1c as an index for diabetes can be determined accurately and easily. Therefore, the determination of HbA1c can be made practice in clinical tests etc.

What is claimed:

1. An isolated enzyme that specifically releases an amino acid having a glycated α-amino group from a glycated protein or a glycated peptide, wherein the enzyme is derived from *Corynebacterium ureolyticum* KDK1002 (FERM P-17135) or *Pseudomonas alcaligenes* KDK1001 (FERM P-17133).

2. An enzyme according to claim 1, wherein the amino acid having a glycated α-amino group to be released is valine having a glycated α-amino group.

3. A kit for determining a glycated protein or a glycated peptide comprising:

a protease;

a fructosyl amino acid oxidase;

a peroxidase; and a substrate that is oxidized through a reaction with the peroxidase, wherein the protease comprises an enzyme according to claim 1.

4. A method of determining a glycated protein or a glycated peptide comprising:

degrading a glycated protein or a glycated peptide with an enzyme to give a degradation product;

causing a redox reaction between the degradation product and a fructosyl amino acid oxidase; and determining the redox reaction so as to determine the amount of the glycated protein or the glycated peptide, wherein the enzyme is an isolated enzyme derived from *Corynebacterium ureolyticum* KDK1002 (FERM P-171351 or *Pseudomonas alcaligenes* KDK1001 (FERM P-17133) that releases an amino acid having a glycated α-amino group from a glycated protein or a glycated peptide.

5. A method according to claim 4, wherein the glycated protein to be determined is glycated hemoglobin.

* * * * *